(12) United States Patent
Maitra et al.

(10) Patent No.: US 10,023,919 B2
(45) Date of Patent: Jul. 17, 2018

(54) METHODS OF IDENTIFYING AND QUANTIFYING BACTERIA IN CHEWING GUM

(71) Applicant: WM. WRIGLEY JR. COMPANY, Chicago, IL (US)

(72) Inventors: Amarnath Maitra, Glen Ellyn, IL (US); David Morando, Whiting, IN (US)

(73) Assignee: WM. WRIGLEY JR. COMPANY, Chicago, IL (US)

( * ) Notice: Subject to any disclaimer, the term of this patent is extended or adjusted under 35 U.S.C. 154(b) by 295 days.

(21) Appl. No.: 14/776,269

(22) PCT Filed: Mar. 13, 2014

(86) PCT No.: PCT/US2014/025430
§ 371 (c)(1),
(2) Date: Sep. 14, 2015

(87) PCT Pub. No.: WO2014/159901
PCT Pub. Date: Oct. 2, 2014

(65) Prior Publication Data
US 2016/0032365 A1    Feb. 4, 2016

Related U.S. Application Data

(60) Provisional application No. 61/783,223, filed on Mar. 14, 2013.

(51) Int. Cl.
*C12Q 1/68* (2018.01)
*C12N 15/10* (2006.01)
*C12Q 1/689* (2018.01)
*C12Q 1/6806* (2018.01)

(52) U.S. Cl.
CPC ......... *C12Q 1/689* (2013.01); *C12N 15/1003* (2013.01); *C12N 15/1006* (2013.01); *C12Q 1/6806* (2013.01); *C12Q 2600/158* (2013.01)

(58) Field of Classification Search
None
See application file for complete search history.

(56) References Cited

U.S. PATENT DOCUMENTS

2004/0185455 A1* 9/2004 Shimada ............... C12Q 1/6853
435/6.12
2010/0029925 A1* 2/2010 Brevnov ............ C12N 15/1013
536/25.41

* cited by examiner

*Primary Examiner* — David C Thomas

(57) ABSTRACT

The invention is directed to methods of extracting nucleic acids from microorganisms or mammalian cells adhered to polymers that are malleable within a living organism and particularly malleable in the oral cavity of the living organism. The invention also provides for method of detecting and quantitating microorganisms that adhere to malleable polymers, such as chewing gum.

18 Claims, 1 Drawing Sheet

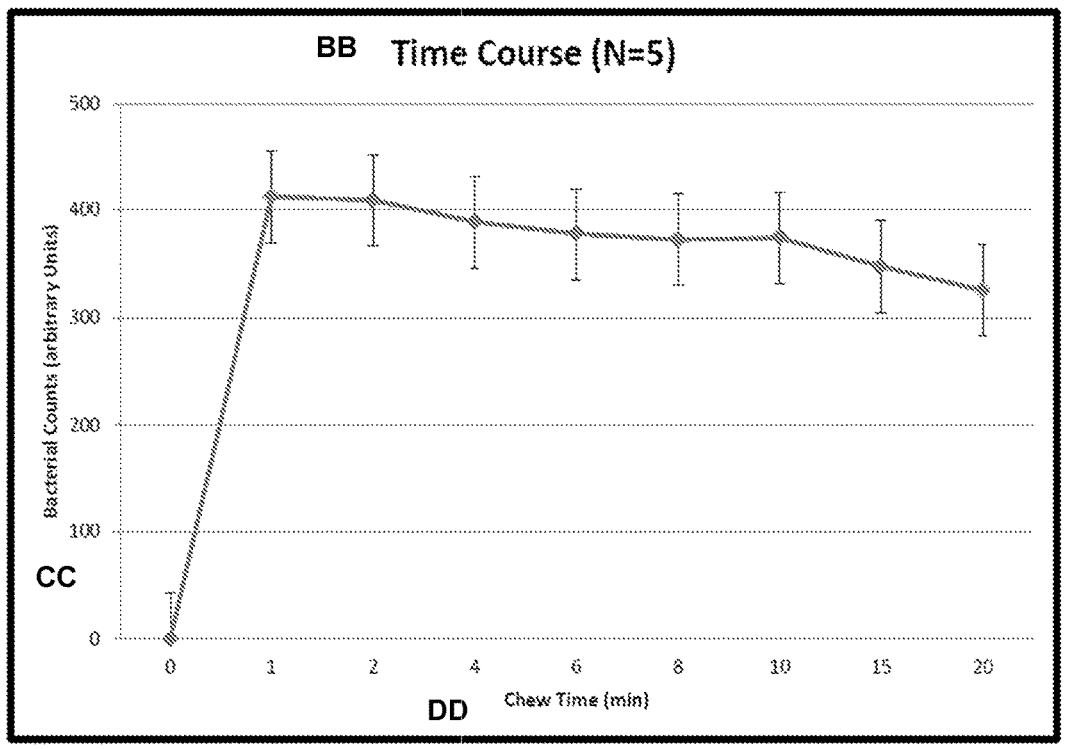

SEQUENCE LISTING

<160> NUMBER OF SEQ ID NOS: 48

<210> SEQ ID NO 1
<211> LENGTH: 23
<212> TYPE: DNA
<213> ORGANISM: Porphyromonas gingivalis

<400> SEQUENCE: 1
cggactaaaa ccgcatacac ttg        23

<210> SEQ ID NO 2
<211> LENGTH: 20
<212> TYPE: DNA
<213> ORGANISM: Porphyromonas gingivalis

<400> SEQUENCE: 2
ggtgagccgt tacctcacca        20

<210> SEQ ID NO 3
<211> LENGTH: 23
<212> TYPE: DNA
<213> ORGANISM: Fusobacterium nucleatum

<400> SEQUENCE: 3
cgcagaaggt gaaagtcctg tat                                    23

<210> SEQ ID NO 4
<211> LENGTH: 23
<212> TYPE: DNA
<213> ORGANISM: Fusobacterium nucleatum

<400> SEQUENCE: 4
tggtcctcac tgattcacac aga                                    23

<210> SEQ ID NO 5
<211> LENGTH: 24
<212> TYPE: DNA
<213> ORGANISM: Fusobacterium nucleatum

<400> SEQUENCE: 5
tgcgataagc ctagataagt tgca                                   24

<210> SEQ ID NO 6
<211> LENGTH: 25
<212> TYPE: DNA
<213> ORGANISM: Fusobacterium nucleatum

<400> SEQUENCE: 6
cttaatagat tgctccattc ggaaa                                  25

<210> SEQ ID NO 7
<211> LENGTH: 20
<212> TYPE: DNA
<213> ORGANISM: Tannerella forsythia

<400> SEQUENCE: 7
atcctggctc aggatgaacg                                        20

<210> SEQ ID NO 8
<211> LENGTH: 19
<212> TYPE: DNA
<213> ORGANISM: Tannerella forsythia

<400> SEQUENCE: 8
tacgcatacc catccgcaa                                         19

<210> SEQ ID NO 9
<211> LENGTH: 19
<212> TYPE: DNA
<213> ORGANISM: Tannerella forsythia

<400> SEQUENCE: 9
gtaacctgcc cgcaacaga                                         19

<210> SEQ ID NO 10
<211> LENGTH: 20
<212> TYPE: DNA
<213> ORGANISM: Tannerella forsythia

<400> SEQUENCE: 10
tgcggaaccc ctgttttatg                                        20

<210> SEQ ID NO 11
<211> LENGTH: 22
<212> TYPE: DNA
<213> ORGANISM: Treponema denticola

```
<400> SEQUENCE: 11
agagcaagct ctcccttacc gt                                            22

<210> SEQ ID NO 12
<211> LENGTH: 22
<212> TYPE: DNA
<213> ORGANISM: Treponema denticola

<400> SEQUENCE: 12
taagggcggc ttgaaataat ga                                            22

<210> SEQ ID NO 13
<211> LENGTH: 25
<212> TYPE: DNA
<213> ORGANISM: Treponema denticola

<400> SEQUENCE: 13
taataccgaa tgtgctcatt tacat                                         25

<210> SEQ ID NO 14
<211> LENGTH: 27
<212> TYPE: DNA
<213> ORGANISM: Treponema denticola

<400> SEQUENCE: 14
tcaaagaagc attccctctt cttctta                                       27

<210> SEQ ID NO 15
<211> LENGTH: 20
<212> TYPE: DNA
<213> ORGANISM: Lactobacillus salivarius

<400> SEQUENCE: 15
agccgatgaa ggacgtgact                                               20

<210> SEQ ID NO 16
<211> LENGTH: 27
<212> TYPE: DNA
<213> ORGANISM: Lactobacillus salivarius

<400> SEQUENCE: 16
ggaaatctcc ggatcatagt ttactta                                       27

<210> SEQ ID NO 17
<211> LENGTH: 17
<212> TYPE: DNA
<213> ORGANISM: Streptococcus mutans

<400> SEQUENCE: 17
tgggacgcaa gggaaca                                                  17

<210> SEQ ID NO 18
<211> LENGTH: 18
<212> TYPE: DNA
<213> ORGANISM: Streptococcus mutans

<400> SEQUENCE: 18
cccgttcgcg actcaaga                                                 18

<210> SEQ ID NO 19
<211> LENGTH: 22
<212> TYPE: DNA
```

```
<213> ORGANISM: Streptococcus mutans

<400> SEQUENCE: 19
tcgcgaaaaa gataaacaaa ca                                        22

<210> SEQ ID NO 20
<211> LENGTH: 20
<212> TYPE: DNA
<213> ORGANISM: Streptococcus mutans

<400> SEQUENCE: 20
gccccttcac agttggttag                                           20

<210> SEQ ID NO 21
<211> LENGTH: 26
<212> TYPE: DNA
<213> ORGANISM: Streptococcus sobrinus

<400> SEQUENCE: 21
ggacttgctc cagtgttact aatgag                                    26

<210> SEQ ID NO 22
<211> LENGTH: 20
<212> TYPE: DNA
<213> ORGANISM: Streptococcus sobrinus

<400> SEQUENCE: 22
ccgctatcag gcaggttacc                                           20

<210> SEQ ID NO 23
<211> LENGTH: 19
<212> TYPE: DNA
<213> ORGANISM: Aggregatibacter actinomycetemcomitans

<400> SEQUENCE: 23
attggggttt agccctggt                                            19

<210> SEQ ID NO 24
<211> LENGTH: 19
<212> TYPE: DNA
<213> ORGANISM: Aggregatibacter actinomycetemcomitans

<400> SEQUENCE: 24
ggcacaaacc catctctga                                            19

<210> SEQ ID NO 25
<211> LENGTH: 22
<212> TYPE: DNA
<213> ORGANISM: Aggregatibacter actinomycetemcomitans

<400> SEQUENCE: 25
ctaggtattg cgaaacaatt tg                                        22

<210> SEQ ID NO 26
<211> LENGTH: 21
<212> TYPE: DNA
<213> ORGANISM: Aggregatibacter actinomycetemcomitans

<400> SEQUENCE: 26
cctgaaatta agctggtaat c                                         21

<210> SEQ ID NO 27
<211> LENGTH: 23
```

```
<212> TYPE: DNA
<213> ORGANISM: Aggregatibacter actinomycetemcomitans

<400> SEQUENCE: 27
atggttgtag gcaatggaag aac                                    23

<210> SEQ ID NO 28
<211> LENGTH: 22
<212> TYPE: DNA
<213> ORGANISM: Aggregatibacter actinomycetemcomitans

<400> SEQUENCE: 28
cacctgagct acagacccaa ca                                     22

<210> SEQ ID NO 29
<211> LENGTH: 20
<212> TYPE: DNA
<213> ORGANISM: Streptococcus salivarius

<400> SEQUENCE: 29
gcagcagtag cagagacgct                                        20

<210> SEQ ID NO 30
<211> LENGTH: 20
<212> TYPE: DNA
<213> ORGANISM: Streptococcus salivarius

<400> SEQUENCE: 30
cacggacgtc ttcagtactg                                        20

<210> SEQ ID NO 31
<211> LENGTH: 23
<212> TYPE: DNA
<213> ORGANISM: Prevotella intermedia

<400> SEQUENCE: 31
gtggcgcgta ttttatgtat gtg                                    23

<210> SEQ ID NO 32
<211> LENGTH: 19
<212> TYPE: DNA
<213> ORGANISM: Prevotella intermedia

<400> SEQUENCE: 32
atccgccata cgcccttag                                         19

<210> SEQ ID NO 33
<211> LENGTH: 21
<212> TYPE: DNA
<213> ORGANISM: Actinomyces naeslundii

<400> SEQUENCE: 33
tcgaaactca gcaagtagcc g                                      21

<210> SEQ ID NO 34
<211> LENGTH: 21
<212> TYPE: DNA
<213> ORGANISM: Actinomyces naeslundii

<400> SEQUENCE: 34
agaggagggc cacaaaagaa a                                      21

<210> SEQ ID NO 35
```

```
<211> LENGTH: 18
<212> TYPE: DNA
<213> ORGANISM: Unknown
<220> FEATURE:
<223> OTHER INFORMATION: Actinomycetes

<400> SEQUENCE: 35
ggatgagccc gcggccta                                                 18

<210> SEQ ID NO 36
<211> LENGTH: 22
<212> TYPE: DNA
<213> ORGANISM: Unknown
<220> FEATURE:
<223> OTHER INFORMATION: Actinomycetes

<400> SEQUENCE: 36
cggccgcggc tgctggcacg ta                                            22

<210> SEQ ID NO 37
<211> LENGTH: 23
<212> TYPE: DNA
<213> ORGANISM: Unknown
<220> FEATURE:
<223> OTHER INFORMATION: Fusobacterium

<400> SEQUENCE: 37
cgcagaaggt gaaagtcctg tat                                           23

<210> SEQ ID NO 38
<211> LENGTH: 23
<212> TYPE: DNA
<213> ORGANISM: Unknown
<220> FEATURE:
<223> OTHER INFORMATION: Fusobacterium

<400> SEQUENCE: 38
tggtcctcac tgattcacac aga                                           23

<210> SEQ ID NO 39
<211> LENGTH: 18
<212> TYPE: DNA
<213> ORGANISM: Unknown
<220> FEATURE:
<223> OTHER INFORMATION: Prevotella

<400> SEQUENCE: 39
ccagccaagt agcgtgca                                                 18

<210> SEQ ID NO 40
<211> LENGTH: 20
<212> TYPE: DNA
<213> ORGANISM: Unknown
<220> FEATURE:
<223> OTHER INFORMATION: Prevotella

<400> SEQUENCE: 40
tggaccttcc gtattaccgc                                               20

<210> SEQ ID NO 41
<211> LENGTH: 21
<212> TYPE: DNA
<213> ORGANISM: Unknown
<220> FEATURE:
<223> OTHER INFORMATION: Veillonella

<400> SEQUENCE: 41
```

```
ccgtgatggg atggaaactg c                                              21

<210> SEQ ID NO 42
<211> LENGTH: 21
<212> TYPE: DNA
<213> ORGANISM: Unknown
<220> FEATURE:
<223> OTHER INFORMATION: Veillonella

<400> SEQUENCE: 42
ccttcgccac tggtgttctt c                                              21

<210> SEQ ID NO 43
<211> LENGTH: 20
<212> TYPE: DNA
<213> ORGANISM: Unknown
<220> FEATURE:
<223> OTHER INFORMATION: Streptococcus

<400> SEQUENCE: 43
agagtttgat cctggctcag                                                20

<210> SEQ ID NO 44
<211> LENGTH: 24
<212> TYPE: DNA
<213> ORGANISM: Unknown
<220> FEATURE:
<223> OTHER INFORMATION: Streptococcus

<400> SEQUENCE: 44
gtaccgtcac agtatgaact ttcc                                           24

<210> SEQ ID NO 45
<211> LENGTH: 21
<212> TYPE: DNA
<213> ORGANISM: Unknown
<220> FEATURE:
<223> OTHER INFORMATION: Lactobacillus

<400> SEQUENCE: 45
ctcaaaacta aacaaagttt c                                              21

<210> SEQ ID NO 46
<211> LENGTH: 20
<212> TYPE: DNA
<213> ORGANISM: Unknown
<220> FEATURE:
<223> OTHER INFORMATION: Lactobacillus

<400> SEQUENCE: 46
cttgtacaca ccgcccgtca                                                20

<210> SEQ ID NO 47
<211> LENGTH: 17
<212> TYPE: DNA
<213> ORGANISM: Artificial Sequence
<220> FEATURE:
<223> OTHER INFORMATION: Synthetic primer

<400> SEQUENCE: 47
cctacgggag gcagcag                                                   17

<210> SEQ ID NO 48
<211> LENGTH: 17
<212> TYPE: DNA
```

```
<213> ORGANISM: Artificial Sequence
<220> FEATURE:
<223> OTHER INFORMATION: Synthetic primer

<400> SEQUENCE: 48
attaccgcgg ctgctgg                                                17
```

METHODS OF IDENTIFYING AND QUANTIFYING BACTERIA IN CHEWING GUM

PRIORITY DATA

The present patent application is a 371 of International Application Ser. No. PCT/US14/25430 filed Mar. 13, 2014, which claims benefit from Ser. No. 61/783,223 filed Mar. 14, 2013. The applications listed above are incorporated by reference from as if entirely restated herein.

FIELD OF INVENTION

The invention provides for methods of extracting nucleic acids from microorganisms or mammalian cells adhered to or entrapped within polymers that are malleable within a living organism and particularly polymers that are malleable in the oral cavity of the living organism. The invention also provides for method of detecting and quantitating microorganisms that adhered to or are entrapped within malleable polymers, such as chewing gum.

BACKGROUND

Descriptions of the first use of chewing gum date back to the ancient Greek, where people used tree resins from the mastic tree to quench thirst or freshen ones breath. The first chewing gum was not successfully marketed until the late 19th century, when the rubbery tree sap of the *Sapodilla* tree formed the basis of the gum. In the late 20th century, chewing gum is not only regarded as a symbol of life style, but also effects on cognitive performance, mood, alertness and appetite control have been reported. Moreover, chewing gum has developed more towards a oral care and functional food product ("nutriceutical") as it provides an easily applicable drug delivery vehicle with potential benefits for oral health. High consumption rates, up to 2.5 kg per person per year, have made it into a billion dollar industry.

Generally, chewing gums consist of a water insoluble mixture of synthetic elastomers, like polyvinyl acetate or polyisobutylene, generally referred to as the gum-base. Important requirements to gum-base materials are that they do not dissolve in the mouth and can be chewed for long periods of time without undergoing compositional changes. In all commercially available chewing gums, the gum-base is supplemented with structuring, softening and flavoring agents, while nowadays sugar is frequently replaced by artificial sweeteners such as sorbitol, xylitol or mannitol.

The inclusion of xylitol and other artificial sweeteners has been described to reduce the formation of oral biofilms on teeth. Oral biofilms are causative to the world's most widespread infectious diseases, namely caries and periodontal disease. Caries arise from an imbalance between naturally occurring de- and remineralization of dental enamel. Demineralization occurs when the pH of oral biofilm drops below 5.5 due to the fermentation of sugars by selected members of oral biofilms on teeth. Most artificial sugars are not or barely fermented by oral bacteria and therewith do not lower the pH. Moreover, chewing gum yields enhanced mastication that stimulates saliva production, therewith increasing the concentrations of calcium and phosphates in the oral cavity required for remineralization. Fluorides have been added to commercial gums to prevent enamel demineralization and stimulate remineralization. It is tempting to regard the chewing of gum as an addendum to daily oral hygiene procedures, especially since most people have through the ages been unable to maintain a level of oral biofilm control required to prevent disease. This has led to the incorporation of antimicrobials like chlorhexidine and herbal extracts to chewing gums and gums have indeed been demonstrated successful in preventing re-growth of oral biofilm. Although it is known that chewing of gum aids removal of interdental debris (Kakodkar et al. Dental Research Journal 7: 64-69, 2011) and detergents like polyphosphates have been added to gums to increase their cleaning power, it is unclear whether chewing of gum will actually remove bacteria from the oral cavity. Especially the preferential removal of disease causing organisms like acid-producing *Streptococcus mutans* or species that are regarded as initial colonizers to the dental enamel by chewing gum would turn chewing gum into a valuable addendum to daily oral hygiene procedures.

The human oral cavity contains a varied and vast amount of flora, and many diseases of the gastrointestinal system and respiratory system can manifest in the oral cavity. There are also many diseases that are specific to the oral cavity. In addition to bacterial organisms, oral microorganisms can include fungal, protozoal, and viral species and many of these microorganisms adhere to the teeth, the gingival sulcus, the tongue, and the buccal mucosa. Each site has a unique way of allowing the organisms to establish their residency. Many of these microorganisms may adhere to polymers that they contact while in the oral cavity, and these polymers include dental and periodontal apparatus and compositions in addition to chewing gum as described above.

Therefore, there is a need for the development of new methods to detect, identify and quantify the numbers of microorganisms that adhere to or are entrapped within polymers in the oral cavity, such as bacteria that are trapped into a chewing gum after use.

SUMMARY OF INVENTION

Chewing gum is known to contribute towards maintenance of oral health; however it is unclear whether gum can actually remove bacteria and other microorganisms from the oral cavity. The present invention provides a method for detecting and quantitating nucleic acids from microorganisms that are adhered to the external surface and/or entrapped within the internal surface of a malleable polymer within the oral cavity of a living organism, such as chewing gum, using an amplification method such as quantitative polymerase chain reaction (PCR). The studies provided herein describe a method by which the number of bacteria trapped in gum after chewing (in vitro or in vivo) were quantified and qualified The invention provides for methods of extracting nucleic acids from a polymer that is malleable within a living organism comprising a) contacting the polymer with i) an organic solvent and ii) buffer solution, and b) separating the organic solvent and a buffer solution, wherein nucleic acid extracted from the polymer are contained within the buffer solution. The invention contemplates carrying out the method of extracting nucleic acids from a polymer after the polymer was in contact with a living organism. The method may be carried out in vitro or outside of the living organism.

These methods may further comprise a step of identifying the source of the nucleic acid extracted from the polymer and/or a step of quantifying the nucleic acid extracted from the polymer. The identifying step or quantifying step is carried out using an amplification method such as polymerase chain reaction, stand displacement, ligase chain reaction, helicase-dependent amplification, isothermal reverse transcription-thermophilic helicase-dependent amplification, rolling circle amplification, loop-mediated isothermal amplification and sequence based amplification.

The methods of the invention extract nucleic acids from polymers that are malleable in a living organism, e.g. malleable in the oral cavity of the living organism. The term "malleable in living organism" refers to polymers that are flexible and pliable at the temperature and pH within a living organism but the composition of the polymer is stable when exposed to varying forces and conditions (e.g. temperature, pH, enzymes) applied by the organism. For example, the method of the invention include polymers that are malleable in response to force applied by the organism (e.g. chewing, grinding or gnashing of the teeth or gums), the temperature in organism (e.g. the temperature of the oral cavity of the organism) or chemical conditions (e.g. enzymes produced by the organism, pH of the oral cavity of the living organism). These malleable polymers may be organic (having a carbon base) and therefore these polymers will dissolve in organic solvents according to the method so the invention. An example of such a polymer includes chewing gum, bubble gum or gum base.

In one embodiment, the malleable polymer used in any of the methods of the invention is an elastomer such as polyvinyl acetate, polybutylene, polyisobutylene, isobutylene-isoprene copolymer (butyl elastomer), styrene-butadiene, styrene-butadiene copolymers, polyvinyl acetate, polyisoprene, polyethylene, vinyl acetate-vinyl laurate copolymer, silicone, jelutong, chicle, sorva and massaranduba balata or combinations thereof.

In another embodiment, the malleable polymer used in any of the methods of the invention is within a dental or periodontal composition, apparatus or device. For example, the malleable polymers may be dental resins or polymers contained on or within endodontic (dental) or periodontal instruments or compositions such as polymers used in mouth guards, fillings, dentures, bridges, crowns, root canals, dental inlays, dental outlays and veneers. In addition, the malleable polymer is on or within surgical devices (e.g. stents or supports), maxillofacial appliances such as cleft palate plates, maxillary supports and orthodontic appliances. These malleable polymers are methyl methacrylate, polymethyl methacrylate (PMMA), polyethyl methacrylate (PEMA), glycidyl methacrylate (GMA), triethylene glycol-dimethacrylate (TEGDMA), bisphenol A-glycidyl methacrylate (BIS-GMA), gutta percha and polybutylene, including alpha-butylene, cis-butylene, beta-butylene, trans-beta-butylene, isobutylene, nylon, and biodegradable polymers such as polylactides (PLA) or combinations thereof.

In any of the methods of the invention, the nucleic acids are extracted from the polymer using an organic solvent and a buffered solution. The term "organic solvent" refers to carbon-based solvents that are capable dissolving or dispersing one or more other substances. Any of the methods of the invention may be carried out with an organic solvent such as chloroform, xylene, toluene, 1,2 dichlorobenzene, hexane, tetrahydrofuran, dichloromethane or acetone.

The term "buffered solution" refers to an aqueous solution that consists of a mixture of a weak acid and its conjugate base or a weak base and its conjugate acid in order to keep the pH of a solution nearly constant. Any of the methods of the invention can be carried out with any buffered solution that is conventional in the field of molecular biology and in which nucleic acids are stable, such as Tris buffer, TBE buffer (Tris-borate-EDTA) and TAE buffer (Tris-acetate-EDTA). In a particular embodiment, the buffered solution is Tris buffer which comprised tris(hydroxymethyl)aminomethane. Tris buffer is also known as Tris base, Trizma, Trisamine, THAM, Tromethamine, Trometamol and Tromethane.

In any of the methods of the invention, the polymer may be partially or completely dissolved by the organic solvent.

In any of the method of the invention, the nucleic acids are extracted from an internal surface of the polymer. The invention also provides for method of extracting nucleic acids from the polymer wherein at least about 99% of the nucleic acids adhered to or entrapped within the polymers are extracted, at least about 98% of the nucleic acids adhered to or entrapped within the polymer are extracted, at least about 95% of the nucleic acids adhered to or entrapped within the polymer are extracted, at least about 90% of the nucleic acids adhered to or entrapped within the polymer are extracted, at least about 85% of the nucleic acids adhered to or entrapped within the polymer are extracted, at least about 80% of the nucleic acids adhered to or entrapped within the polymer are extracted, at least about 75% of the nucleic acids adhered to or entrapped within the polymer are extracted, at least about 60% of the nucleic acids adhered to or entrapped within the polymer are extracted, at least about 55% of the nucleic acids adhered to or entrapped within the polymer are extracted or at least about 50% of the nucleic acids adhered to or entrapped within the polymer are extracted.

In one embodiment, the invention provides for methods of extracting nucleic acids from microorganisms adhered to or entrapped within the polymers, including microorganism entrapped within the internal surface of the polymer or microorganism adhered to or entrapped within the external surface of the polymer. For example, the invention provides for methods wherein the source of the nucleic acid is a bacteria, virus, fungus or protozoa. In particular, the source of the nucleic acids may be pathogenic or commensal bacteria of the oral cavity such as *Streptococcus mutans, Streptococcus oralis, Actinomyces naeslundii, Streptococcus sanguinis, Porphyromomas gingivalis, Porphymomas intermedia, Bacteroides forsythus, Tanneraella forsythia, Campylobacter rectus, Eubacerium nodatum, Peptostreptococcus micros, Streptococcus intermedius, Aggregetibacter actinomycetemcomitans, Treponema denticola, Eikenella corrodens, Capnocytophaga gingivalis, Streptococcus gordonii, Veillonella parvula, Fusobacterium nucleatum, Prevotella intermedia, Lactobacillus salivarius, Streptococcus salivarius* and *Streptoococus sobrinus*.

In another embodiment, the invention provides for methods of extracting nucleic acids from mammalian cells, such as human cells, canine cells, feline cells, murine cells, rat cells, bovine cells, equine cells, sheep cells, goat cells, primate cells, cells from aquatic mammals such as whales and dolphins and cells from other exotic mammals. For example, the invention provides for methods wherein the source of the nucleic acids is an epithelial cell, squamous cell, fibroblast, stem cell or keratocyte. The invention also provides for methods of extracting nucleic acids from cancer cells.

Another aspect of the invention is methods of detecting a microorganism adhered to or entrapped within a polymer malleable in a living organism comprising a) dissolving at least a portion of the polymer in an organic solvent and a buffered solution, b) separating the organic solvent and buffered solution, wherein nucleic acid extracted from the microorganisms are contained within the buffer solution, and c) amplifying the nucleic acids using at least one oligonucleotide primer specific for the microorganism. Further, the methods may be carried out with two or more primers, three or more primers. In this method, the microorganism detected may be adhered to, or entrapped within the external surface of the polymer or entrapped within the internal surface of the polymer. The invention contemplates carrying out the method of detecting microorganism adhered to or entrapped within a polymer after the polymer was in contact with a living organism. The methods are carried out in vitro or outside of the living organism. These methods may be carried out for quality control purposes, e.g. working in the fields of food safety, food spoilage and fermentation; and for the microbial risk assessment for polymers in contact with food, such as polymers in packaging. These methods may also be carried out for diagnosing an infection, disease, disorder or condition of the oral cavity of a subject, for determining the susceptibility of a subject for developing a disease, disorder or condition, or for generating a microbe profile of a subject.

The amplification step of these methods may be carried out using any method known in the art. For example, the nucleic acids of the microorganism adhered to or entrapped within the polymer may be amplified using polymerase chain reaction, stand displacement, ligase chain reaction, helicase-dependent amplification, isothermal reverse transcription-thermophilic helicase-dependent amplification, rolling circle amplification, loop-mediated isothermal amplification, sequence based amplification or sequence based amplification.

These methods may further comprise a step of quantifying the number of microorganisms adhered to or entrapped within the polymer. The identifying step or quantifying step is carried out using an amplification method such as polymerase chain reaction, stand displacement, ligase chain reaction, helicase-dependent amplification, isothermal reverse transcription-thermophilic helicase-dependent amplification, rolling circle amplification, loop-mediated isothermal amplification or sequence based amplification.

The invention provides for methods of detecting a microorganism adhered to or entrapped within a polymer malleable in a living organism such as chewing gum, bubble gum or gum base. These malleable polymers may be organic (having a carbon base) and therefore these polymers will dissolve in organic solvents according to the method so the invention. In one embodiment, the malleable polymer is an elastomer such as polyvinyl acetate, polybutylene, polyisobutylene, isobutylene-isoprene copolymer (butyl elastomer), styrene-butadiene copolymers, polyvinyl acetate, polyisoprene, polyethylene, vinyl acetate-vinyl laurate copolymer, silicone, jelutong, chicle, sorva and massaranduba balata or combinations thereof.

In another embodiment, the malleable polymer in which the microorganism is adhered or entrapped may be within a dental or periodontal composition, apparatus or device. For example, the malleable polymers may be dental resins or polymers contained on or within endodontic (dental) or periodontal instruments or compositions such as polymers used in fillings, dentures, bridges, crowns, root canals, dental inlays, dental outlays and veneers. In addition, the malleable polymer is on or within surgical devices (e.g. stents or supports), maxillofacial appliances such as cleft palate plates, maxillary supports and orthodontic appliances. These malleable polymers are methyl methacrylate, polymethyl methacrylate (PMMA), polyethyl methacrylate (PEMA), glycidyl methacrylate (GMA), triethylene glycol-dimethacrylate (TEGDMA), bisphenol A-glycidyl methacrylate (BIS-GMA), gutta percha and polybutylene, including alpha-butylene, cis-butylene, beta-butylene, trans-beta-butylene, isobutylene, silicone, nylon and biodegradable polymers such as polylactides or combination thereof.

In the methods of detecting a microorganism adhered to or entrapped within a polymer malleable in a living organism, the polymer is dissolved in an organic solvent such chloroform, xylene or toluene, and a buffered solution that is conventional in the field of molecular biology and in which nucleic acids are stable, such as Tris buffer, TBE buffer (Tris-borate-EDTA) and TAE buffer (Tris-acetate-EDTA). In a particular embodiment, the Tris buffer comprised tris(hydroxymethyl)aminomethane. Tris buffer is also known as Tris base, Trizma, Trisamine, THAM, Tromethamine, Trometamol and Tromethane.

The invention provides for methods of detecting any type of microorganism including bacteria, virus, fungus and protozoa. For example, the invention provides for methods of detecting pathogenic or commensal bacteria present in the oral cavity such as *Streptococcus mutans, Streptococcus sanguinis, Streptococcus salivarius, Porphyromomas gingivalis, Porphymomas intermedia, Actinomyces naeslundii, Bacteroides forsythus, Tannerella forsythia, Campylobacter rectus, Eubacerium nodatum, Peptostreptococcus micros, Streptococcus intermedius, Aggregetibacter actinomycetemcomitans, Treponema denticola, Eikenella corrodens, Capnocytophaga gingivalis, Streptococcus gordonii, Veillonella parvula, Streptococcus oralis, Fusobacterium nucleatum, Prevotella intermedia, Lactobacillus salivarius, Streptococcus salivarius* and *Streptoococus sobrinus*. Optionally, the method may further comprise the step of diagnosing a bacterial infection in a mammalian subject, such as a human subject, by detecting the presence of the bacteria adhered to or entrapped within a malleable polymer that was contacted with the oral cavity of the mammalian subject. The methods also may optionally comprise the step of informing the human subject of the presence of the bacteria or the diagnosis of a bacterial infection in the oral cavity.

The invention also provides for an in vitro method of diagnosing a bacterial infection in the oral cavity of a mammalian subject comprising detecting a bacteria adhered to or entrapped within a polymer according to any of the preceding methods wherein the polymer was in contact with the oral cavity of subject, and wherein the presence of the bacteria adhered to or entrapped in the polymer is indicative of a bacterial infection in the oral cavity of the subject.

The invention also provides for an in vitro method of determining the susceptibility of a mammal subject for developing a bacterial infection in the oral cavity comprising detecting a bacteria adhered to or entrapped within a polymer according to any of the preceding methods wherein the polymer was in contact with the oral cavity of the subject, and wherein the presence of the bacteria adhered to or entrapped within the polymer is indicative of increased susceptibility for developing a bacterial infection in the oral cavity of the subject or increases susceptibility of developing a disease, condition or disorder associated with the presence of the bacteria in the oral cavity of the subject.

In addition, the invention provides for method of detecting virus present in the oral cavity such as Human Herpes Virus (HHV)-1 (also known as herpes simplex virus (HSV)-1, HHV-2 (HSV-2), HHV-3 (also known as Varicella-zoster virus), HHV-4 (Epstein-Barr virus), HHV-5 (cytomegalovirus), HHV-6, HHV-7, HHV-8, poliovirus, group A coxsackievirus, group B coxsackievirus, echovirus and *Enterovirus* 71 (EV-71), Human Papillomavirus family (HPV), e.g. HPV-16, HPV-18, HPV-33, HPV-35, mumps virus, Newcastle disease virus, human parainfluenza virus type 2, 4a and 4, Paramyxovirus, Rubivirus, human influenza virus A, e.g. H1N1 and H3N3, human influenza virus B, human influenza virus C, rhinovirus, canine oral Papilloma virus, feline calicivirus, and feline herpesvirus. Optionally, the method may further comprise the step of diagnosing a viral infection in a mammal, such as a human subject, by detecting the presence of the virus adhered to or entrapped within a malleable polymer that was contacted with the oral cavity of the mammal. The methods also may optionally comprise the step of informing the human subject of the presence of the virus or the diagnosis of a viral infection in the oral cavity.

The invention also provides for an in vitro method of diagnosing a viral infection in the oral cavity of a mammalian subject comprising detecting a virus adhered to or entrapped within a polymer according to any of the preceding methods wherein the polymer was in contact with the oral cavity of subject, and wherein the presence of the virus adhered to or entrapped in the polymer is indicative of a viral infection in the oral cavity of the subject.

The invention also provides for an in vitro method of determining the susceptibility of a mammal subject for developing a viral infection in the oral cavity comprising detecting a virus adhered to or entrapped within a polymer according to any of the preceding methods wherein the polymer was in contact with the oral cavity of the subject, and wherein the presence of the virus adhered to or entrapped within the polymer is indicative of increased susceptibility for developing a viral infection in the oral cavity of the subject or increases susceptibility of developing a disease, condition or disorder associated with the presence of the virus in the oral cavity of the subject.

Further, the invention provides for methods of detecting the presence of a fungus in the oral cavity. The methods of the invention may detect a fungus such as *Candida* e.g. *Candida albicans, Aspergillus, Cryptococcus neoformans, Cryptococcus gattii, Histoplasma capsulatum, Blastomyces dermatitidis, Paracoccidioides brasiliensis, Coccidiodes immites* and *Zygomycota*. Optionally, the method may further comprise the step of diagnosing a fungal infection in a mammal, such as a human subject, by detecting the presence of the fungus adhered to or entrapped within a malleable polymer that was contacted with the oral cavity of the mammal. The methods also may optionally comprise the step of informing the human subject of the presence of the fungus or the diagnosis of a fungal infection in the oral cavity.

The invention also provides for an in vitro method of diagnosing a fungal infection in the oral cavity of a mammalian subject comprising detecting a fungus adhered to or entrapped within a polymer according to any of the preceding methods wherein the polymer was in contact with the oral cavity of subject, and wherein the presence of the fungus adhered to or entrapped in the polymer is indicative of a fungal infection in the oral cavity of the subject.

The invention also provides for an in vitro method of determining the susceptibility of a mammal subject for developing a fungal infection in the oral cavity comprising detecting a fungus adhered to or entrapped within a polymer according to any of the preceding methods wherein the polymer was in contact with the oral cavity of the subject, and wherein the presence of the fungus adhered to or entrapped within the polymer is indicative of increased susceptibility for developing a fungal infection in the oral cavity of the subject or increases susceptibility of developing a disease, condition or disorder associated with the presence of the bacteria in the oral cavity of the subject.

The invention also provides for methods of detecting the presence of protozoa in the oral cavity such as *Entamoeba gingivalis* and *Trichomonas tenax*. Optionally, the method may further comprise the step of diagnosing a protozoan infection in a mammal, such as a human subject, by detecting the presence of the protozoa adhered to or entrapped within a malleable polymer that was contacted with the oral cavity of the mammal. The methods also may optionally comprise the step of informing the human subject of the presence of the protozoa or the diagnosis of a protozoan infection in the oral cavity.

The invention also provides for an in vitro method of diagnosing a protozoan infection in the oral cavity of a mammalian subject comprising detecting a protozoa adhered to or entrapped within a polymer according to any of the preceding methods wherein the polymer was in contact with the oral cavity of subject, and wherein the presence of the protozoa adhered to or entrapped in the polymer is indicative of a protozoan infection in the oral cavity of the subject.

The invention also provides for an in vitro method of determining the susceptibility of a mammal subject for developing a protozoan infection in the oral cavity comprising detecting a protozoa adhered to or entrapped within a polymer according to any of the preceding methods wherein the polymer was in contact with the oral cavity of the subject, and wherein the presence of the protozoa adhered to or entrapped within the polymer is indicative of increased susceptibility for developing a bacterial infection in the oral cavity of the subject or increases susceptibility of developing a disease, condition or disorder associated with the presence of the protozoa in the oral cavity of the subject.

Furthermore, the methods of detecting a microorganism adhered to or entrapped within a polymer may be used to diagnose any disease related to a bacterial, viral, fungal or protozoan infection in the oral cavity. Exemplary conditions, diseases and disorders include chronic periodontitis, acute adult periodontitis, gingivitis such as acute necrotizing ulcerative gingivitis, Vincent angina, dental caries, herpesvirus infection, primary herpetic gingivostomatitis or oral herpes (cold sores and canker sores), genital herpes, varicella-zoster virus infection e.g. chicken pox or shingles, influenza, common cold, venereal disease, mononucleosis, coxsackievirus infection such as hand-foot-mouth disease, herpangina, acute lymphonodular pharyngitis, mumps, measles (reubeola), rubella (German measles), African Burkitt lymphoma, nasopharyngeal carcinoma, oral hairy leukoplakia, roseola infantum, Karposi sarcoma, Candidiasis, acute pseudomemranous candidosis (thrush), acute atrophic (erythematous) candidosis, chronic hyperplastic candidosis, chronic atrophic (erythematous) candidosis, aspergillosis, cryptococcosis, histoplasmosis, blastomycosis, paracoccidioidomycosis, and zygomycosis (mucormycosis).

In another aspect, the invention provides for methods of identifying malleable polymers resistant to adherence of a microorganism comprising a) contacting a malleable polymer with a microorganism under conditions that promote attachment, b) dissolving at least a portion of the polymer in organic solvent and buffered solution, b) separating the organic solvent and the buffered solution, wherein nucleic acid extracted from the microorganisms adhered to the polymer are contained within the buffer solution, and c) detecting the presence or absence of nucleic acid specific for a microorganism in the buffer solution, wherein the absence of nucleic acids in the buffered solution is indicative of a polymer that is resistant to the attachment of microorganism.

The invention contemplates carrying out the method of identifying malleable polymers resistant to adherence of a microorganism in vitro or outside of the living organism. These methods may be carried out for quality control purposes or for purposes. The preceding methods can be carried out using any type of polymer that is malleable in a living organism. For example, the malleable polymer may be chewing gum, bubble gum or gum base. In addition, these malleable polymers may be organic (having a carbon base) and therefore these polymers will dissolve in organic solvents according to the method so the invention. In one embodiment, the malleable polymer is an elastomer such as polyvinyl acetate, polybutylene, polyisobutylene, isobutylene-isoprene copolymer (butyl elastomer), styrene-butadiene, styrene-butadiene copolymers, polyvinyl acetate, polyisoprene, polyethylene, vinyl acetate-vinyl laurate copolymer, silicone, jelutong, chicle, sorva and massaranduba balata or combinations thereof.

In another embodiment, the methods are carried out on a malleable polymer on or within a dental or periodontal composition, apparatus or device. For example, the malleable polymers may be dental resins or polymers contained on or within endodontic (dental) or periodontal instruments or compositions such as polymers used in fillings, dentures, bridges, crowns, root canals, dental inlays, dental outlays and veneers. In addition, the malleable polymer is on or within surgical devices (e.g. stents or supports), maxillofacial appliances such as cleft palate plates, maxillary supports and orthodontic appliances. These malleable polymers are methyl methacrylate, polymethyl methacrylate (PMMA), polyethyl methacrylate (PEMA), glycidyl methacrylate (GMA), triethylene glycol-dimethacrylate (TEGDMA), bisphenol A-glycidyl methacrylate (BIS-GMA), gutta percha and polybutylene, including alpha-butylene, cis-butylene, beta-butylene, trans-beta-butylene, isobutylene, silicone, nylon and biodegradable polymers such as polylactides or combinations thereof.

In the preceding methods, at least a portion of the polymer is dissolved in an organic solvent such as chloroform, xylene or toluene, and a buffered solution such as any buffered solution that is conventional in the field of molecular biology and in which nucleic acids are stable, such as Tris buffer, TBE buffer (Tris-borate-EDTA) and TAE buffer (Tris-acetate-EDTA). In a particular embodiment, the buffered solution is Tris buffer which comprised tris(hydroxymethyl) aminomethane. Tris buffer is also known as Tris base, Trizma, Trisamine, THAM, Tromethamine, Trometamol and Tromethane.

The invention provides for methods of identifying malleable polymers resistance to adherence of any type of microorganisms such as bacteria, virus, fungus or protozoa. For example, the invention provide for methods wherein the microorganism testes is a pathogenic or commensal bacteria of the oral cavity such as *Streptococcus mutans, Streptococcus oralis, Actinomyces naeslundii, Streptococcus sanguinis, Porphyromomas gingivalis, Porphymomas intermedia, Bacteroides forsythus, Tanneraella forsythia, Campylobacter rectus, Eubacerium nodatum, Peptostreptococcus micros, Streptococcus intermedius, Aggregetibacter actinomycetemcomitans, Treponema denticola, Eikenella corrodens, Capnocytophaga gingivalis, Streptococcus gordonii, Veillonella parvula, Fusobacterium nucleatum, Prevotella intermedia, Lactobacillus salivarius, Streptococcus salivarius* and *Streptooccus sobrinus*.

Another aspect of the invention provides for methods of generating a microbe profile of the oral cavity of a mammalian subject comprising a) contacting a malleable polymer with the oral cavity of the subject b) detecting the presence and absence of at least one microorganism adhered to or attached to the malleable polymer after contact with the oral cavity of the subject, wherein the presence or absence of at least one microorganism determines the microbe profile of the oral cavity of the subject. The microbe profile may comprise information on at least one microorganism, at least two microorganisms, at least five microorganisms, at least 10 microorganisms, at least 20 microorganisms, at least 50 microorganisms, at least 100 microorganisms and at least 500 microorganisms These methods may optionally further comprise the steps of comparing the microbe profile of the mammalian subject with a reference microbe profile, wherein the reference profile is indicative of increased susceptibility for a disease, disorder or condition of the oral cavity and scoring the microbe profile to determine whether the subject has increased susceptibility for a disease or disorder of the oral cavity. Further, these methods may optionally comprise the step of quantitating the microorganisms adhered to or entrapped within the polymer.

The term "microbe profile" refers to the presence or absence of at least one microbe that is at least partially identified or characterized so that the presence or absence of the microbe in any particular sample may be monitored. The term "reference microbe profile" refers to a microbe profile generated for a known control or standard sample, such as a reference profile for a subject known to have increased susceptibility for a disease, disorder or condition of the oral cavity.

A microbe profile of a subject associates with a reference microbe profile when one or more the microorganisms in the reference profile are present in the microbe profile of the subject. To determine if a subject microbe profile associates with a reference microbe profile, the profiles are scored to compare the subject microbe profile with the reference profile.

The methods of generating a microbe profile may detect one or more of bacteria, virus, fungus or protozoa. For example, the bacteria detected to generate a microbe profile include *Streptococcus mutans, Streptococcus oralis, Actinomyces naeslundii, Streptococcus sanguinis, Porphyromomas gingivalis, Porphymomas intermedia, Bacteroides forsythus, Tanneraella forsythia, Campylobacter rectus, Eubacerium nodatum, Peptostreptococcus micros, Streptococcus intermedius, Aggregetibacter actinomycetemcomitans, Treponema denticola, Lactobacillus, Eikenella corrodens, Capnocytophaga gingivalis, Streptococcus gordonii, Veillonella parvula, Fusobacterium nucleatum*, and *Streptoococus sobrinus*. Exemplary viruses that may be detected to generate a microbe profile include Human Herpes Virus (HHV)-1 (also known as herpes simplex virus (HSV)-1, HHV-2 (HSV-2), HHV-3 (also known as varicella-zoster virus), HHV-4 (Epstein-Ban-virus), HHV-5 (cytomegalovirus), HHV-6, HHV-7, HHV-8, poliovirus, group A coxsackievirus, group B coxsackievirus, echovirus and *Enterovirus* 71 (EV-71), Human Papillomavirus family (HPV), e.g. HPV-16, HPV-18, HPV-33, HPV-35, mumps virus, Newcastle disease virus, human parainfluenza virus type 2, 4a and 4, Paramyxovirus, Rubivirus, human influenza virus A, e.g. H1N1 and H3N3, human influenza virus B, human influenza virus C and rhinovirus. Exemplary funguses that may be detected to generate a microbe profile include *Candida* e.g. *Candida albicans, Aspergillus, Cryptococcus neoformans, Cryptococcus gattii, Histoplasma capsulatum, Blastomyces dermatitidis, Paracoccidioides brasiliensis,* and *Zygomycota*. Exemplary protozoa that may be detected to generate a microbe profile include *Entamoeba gingivalis* and *Trichomonas tenax*.

Furthermore, the microbe profiles of the present invention may be used to determine susceptibility of the subject for developing a disease, condition or disorder such as chronic periodontitis, acute adult periodontitis, gingivitis such as acute necrotizing ulcerative gingivitis, Vincent angina, dental caries, herpesvirus infection, primary herpetic gingivostomatitis or oral herpes (cold sores and canker sores), genital herpes, varicella-zoster virus infection e.g. chicken pox or shingles, influenza, common cold, venereal disease, mononucleosis, coxsackievirus infection such as hand-foot-mouth disease, herpangina, acute lymphonodular pharyngitis, mumps, measles (reubeola), rubella (German measles), African Burkitt lymphoma, nasopharyngeal carcinoma, oral hairy leukoplakia, roseola infantum, Karposi sarcoma, Candidiasis, acute pseudomemranous candidosis (thrush), acute atrophic (erythematous) candidosis, chronic hyperplastic candidosis, chronic atrophic (erythematous) candidosis, aspergillosis, cryptococcosis, histoplasmosis, blastomycosis, paracoccidioidomycosis, and zygomycosis (mucormycosis).

The preceding methods of generating a microbe profile may be carried out using any type of polymer that is malleable in a living organism. For example, the malleable polymer may be chewing gum, bubble gum or gum base. In addition, these malleable polymers may be organic (having a carbon base) and therefore these polymers will dissolve in organic solvents according to the method so the invention. In one embodiment, the malleable polymer is an elastomer such as polyvinyl acetate, polybutylene, polyisobutylene, isobutylene-isoprene copolymer (butyl elastomer), styrene-butadiene, styrene-butadiene copolymers, polyvinyl acetate, polyisoprene, polyethylene, vinyl acetate-vinyl laurate copolymer, silicone, jelutong, chicle, sorva and massaranduba balata or combinations thereof.

In another embodiment, the methods of generating a microbe profile may be carried out on a malleable polymer on or within a dental or periodontal composition, apparatus or device. For example, the malleable polymers may be dental resins or polymers contained on or within endodontic (dental) or periodontal instruments or compositions such as polymers used in fillings, dentures, bridges, crowns, root canals, dental inlays, dental outlays and veneers. In addition, the malleable polymer is on or within surgical devices (e.g. stents or supports), maxillofacial appliances such as cleft palate plates, maxillary supports and orthodontic appliances. These malleable polymers are methyl methacrylate, polymethyl methacrylate (PMMA), polyethyl methacrylate (PEMA), glycidyl methacrylate (GMA), triethylene glycol-dimethacrylate (TEGDMA), bisphenol A-glycidyl methacrylate (BIS-GMA), gutta percha and polybutylene, including alpha-butylene, cis-butylene, beta-butylene, trans-beta-butylene, isobutylene, silicone, nylon and biodegradable polymers such as polylactides or combinations thereof.

In another aspect, the invention provides for kits for carrying out any of the preceding methods described herein. In particular, the invention provides for kits for detecting or quantitating a microorganism adhered to or entrapped within a polymer malleable in a living organism comprising at least one primer specific for the microorganism, an organic solvent and buffered solution.

These kits may optionally comprise an organic solvent such as chloroform, xylene or toluene, and/or a buffered solution that is conventional in the field of molecular biology and in which the nucleic acids are stable, such as Tris buffer, TBE buffer (Tris-borate-EDTA) and TAE buffer (Tris-acetate-EDTA). In a particular embodiment, the buffered solution is Tris buffer which comprised tris(hydroxymethyl)aminomethane. Tris buffer is also known as Tris base, Trizma, Trisamine, THAM, Tromethamine, Trometamol and Tromethane. In addition, the kits of the invention may optionally further comprise buffers for PCR amplification, dNTP's and buffers for gel loading.

DESCRIPTION OF DRAWING

FIG. 1 depicted bacteria trapped in chewed gum in vivo over time. The number of bacteria, expressed either in CFUs (log-units) determined using the calibration curve (A) or arbitrary units as obtained using qPCR (B), trapped in two different gum types as a function of chewing time. Error bars denote the standard deviation over a group of five volunteers measured twice.

DETAILED DESCRIPTION

The invention provides for method of extracting nucleic acids from a microorganism adhered to or entrapped within a polymer that is malleable within a living organism. Polymers that are "malleable in a living organism" are flexible and pliable at the temperature and pH within a living organism but the composition of the polymer is stable when exposed to varying forces and conditions (e.g. temperature, pH, enzymes) applied by the organism. For example, the method of the invention include polymers that are malleable in response to force applied by the organism (e.g. chewing, grinding or gnashing of the teeth or gums), the temperature in organism (e.g. the temperature of the oral cavity of the organism) or chemical conditions (e.g. enzymes produced by the organism, pH of the oral cavity of the living organism). These malleable polymers may be organic (having a carbon base) and therefore these polymers will dissolve in organic solvents according to the method so the invention. An example of such a polymer includes chewing gum, bubble gum or gum base.

Other malleable polymers that are used in the methods of the invention include dental resins or polymers contained on or within endodontic (dental) or periodontal instruments, compositions or apparatus such as polymers used in cavity restoring materials such as composites and fillings, dentures, bridges, crowns, root canals, dental inlays, dental outlays, veneers or surgical devices (e.g. stents and supports), maxillofacial appliances such as cleft palate plates, maxillary supports, orthodontic appliances such as habit (nail biting or thumb sucking) breaking appliances, mouth guards, teeth grinding guards, pacifiers, teats, nipples, drinking spouts teething rings or toys, chew sticks or toys and other chewing devices for humans and animals. Malleable polymers used in food packaging may also be used in the methods of the invention. These polymers include isoprene, methyl methacrylate, polymethyl methacrylate (PMMA), polyethyl methacrylate (PEMA), polybutyl methacrylate (PBMA), glycidyl methacrylate (GMA), bisphenol A-glycidyl methacrylate (BIS-GMA), triethylene glycol-dimethacrylate (TEGDMA), gutta percha and polybutylene. The term "polybutylene" includes alpha-butylene, cis-butylene, beta-butylene, trans-beta-butylene, isobutylene, silicone, nylon and biodegradable polymers such as polylactides or combinations thereof.

Furthermore, the invention provides for method of extracting nucleic acids from a microorganism adhered to or entrapped within a polymer that dissolves in an organic solvent after being in contact with a living organism such as medical devices, dental or periodontal devices and surgical devices.

The methods of the invention may be carried out on polymers commonly used in medical devices. For example, thermoplastic polymers that are commonly used in medical devices including polyethylene, polypropylene, polystyrene, polyester, such as polyethylene terephthalate (PET), polyester such (PLA), polycarbonate (PC), polyvinyl chloride (PVC), polyether sulfone (PES), polyacrylate (PMMA), polysulfone (PSU), polyetheretherketone (PEEK), acrylonitrile butadiene styrene (ABS), polytetrafluoroethylene, polypropylene alloys, homopolymers and copolymers, polyoxymethylene or polyacetal copolymers. The thermoplastic polymers include amorphous thermoplastics and semi-crystalline thermoplastics. In addition, thermoset polymers are commonly used in medical devices such as Hydrogel (acrylate), polyurethane (PUR, TPU). Elastomers such as silicone are also commonly used in medical devices.

The methods of the invention may be carried out on biodegradable polymers including natural, synthetic and biosynthetic polymers such as those used in bioresorbable sutures, stents, pins, rods, and staples for wound closures, tissue engineering scaffolds and soft tissue augmentation, including polyesters such as polylactic acid (PLLA), polylactide (PLA), polyglycolide (PGA), polycaprolactone (PCL). Other bio-degradable polymers include poly(hydroxyalkanoate)s of the PHB-PHV class, additional poly(ester)s, and natural polymers, particularly, modified poly(saccharide)s, e.g., starch, cellulose, and chitosan.

Chewing Gum

Chewing gum generally consists of a water insoluble gum base, a water soluble portion, and flavor. The water soluble portion dissipates with a portion of the flavor of the gum over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 25% to about 35% by weight, of the chewing gum.

For example, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with gel permeation chromatography (GPC) weight average molecular weight of about 10,000 to about 95,000, isobutylene-isoprene copolymer (butyl elastomer), styrene-butadiene, copolymers having styrene-butadiene ratios of about 1:3 to about 3:1, polyvinyl acetate having GPC weight average molecular weight of about 2,000 to about 90,000, polyisoprene, polyethylene, vinyl acetate-vinyl laurate copolymer having vinyl laurate content of about 5% to about 50% by weight of the copolymer, and combinations thereof.

Preferred ranges for polyisobutylene are 50,000 to 80,000 GPC weight average molecular weight and for styrene-butadiene are 1:1 to 1:3 bound styrene-butadiene, for polyvinyl acetate are 10,000 to 65,000 GBC weight average molecular weight with the higher molecular weight polyvinyl acetates typically used in bubble gum base, and for vinyl acetate-vinyl laurate, vinyl laurate content of 10-45%.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids); and combinations thereof. Colorants and whiteners may include FD&C-type dyes and lakes, fruit and vegetable extracts, titanium dioxide, and combinations thereof. The base may or may not include wax.

In addition to a water insoluble gum base portion, a typical chewing gum composition includes a water soluble bulk portion and one or more flavoring agents. The water soluble portion can include bulk sweeteners, high-intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, levulose, galactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High potency sweeteners can also be used, alone or in combination, with the above. Preferred sweeteners include, but are not limited to, sucralose, aspartame, salts of acesulfame, altitame, saccharin and its salts, cyclamic acid and its salts, glycerrhizinate, dihydrochalcones, thaumatin, lo han guao, monellin, stevia and its glycosides and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

Organic Solvents

The method of the invention comprise dissolving the malleable polymer in an organic solvent. Solvents are substances that are capable of dissolving or dispersing one or more other substances. Organic solvents are carbon-based solvents (i.e., they contain carbon in their molecular structure). Exemplary organic solvents that can be used in the methods of the invention include chloroform, xylene, toluene, 1,2 dichlorobenzene, hexane, tetrahydrofuran, dichloromethane or acetone.

Buffers

The term "buffered solution" refers to an aqueous solution that consists of a mixture of a weak acid and its conjugate base or a weak base and its conjugate acid, and which are used to keep the pH of a solution nearly constant. The buffered solution used in the methods of the invention are neutral or mildly basic and keep nucleic acids stable. Exemplary buffers that are used in any of the methods of the invention are set out in Table 1.

The term "Tris buffer" refers to a buffering solution comprising tris(hydroxymethyl)aminomethane. Tris buffer is also known as Tris base, Trizma, Trisamine, THAM, Tromethamine, Trometamol and Tromethane.

The methods of the invention may also be carried out with buffer solutions that comprise Tris such as TAE buffer (Tris-acetate-EDTA, which is a solution containing Tris base, acetic acid and EDTA), or TBE buffer (Tris-borate-EDTA), which contains Tris base, boric acid and EDTA.

Alternatively, the methods of the invention may be carried out with lithium borate buffer (LB) which is a solution containing lithium hydroxide monohydrate and boric acid, or sodium borate buffer (SB).

Nucleic Acids

The term "nucleic acid," "nucleic acid sequence" or "nucleic acid molecule" refers to a DNA or RNA sequence. The term encompasses molecules formed from any of the known base analogs of DNA and RNA such as, but not limited to 4-4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The methods of the invention may detect and/or quantify naturally occurring or "native" nucleic acids or non-naturally occurring, non-native artificial, synthesized or artificial

TABLE 1

Common Biological Buffers

| Common Name | p$K_a$ | Buffer Range | Temperature Effect (dpH/dT in (1/K) | Mol. Wt. | Full Compound Name |
|---|---|---|---|---|---|
| TRIS | 8.07 | 7.5-9.0 | −0.028 | 121.14 | tris(hydroxymethyl)methylamine |
| Tricine | 8.05 | 7.4-8.8 | −0.021 | 179.2 | N-tris(hydroxymethyl)methylglycine |
| TAPS | 8.43 | 7.7-9.1 | −0.018 | 243.3 | 3-{[tris(hydroxymethyl)methyl]amino}propanesulfonic acid |
| TAPSO | 7.635 | 7.0-8.2 | | 259.3 | 3-[N-Tris(hydroxymethyl)methylamino]-2-hydroxypropanesulfonic Acid |
| HEPES | 7.48 | 6.8-8.2 | −0.014 | 238.3 | 4-2-hydroxyethyl-1-piperazineethanesulfonic acid |
| TES | 7.40 | 6.8-8.2 | −0.020 | 229.20 | 2-{[tris(hydroxymethyl)methyl]amino}ethanesulfonic acid |
| MOPS | 7.20 | 6.5-7.9 | −0.015 | 209.3 | 3-(N-morpholino)propanesulfonic acid |
| PIPES | 6.76 | 6.1-7.5 | −0.008 | 302.4 | piperazine-N,N'-bis(2-ethanesulfonic acid) |
| Cacodylate | 6.27 | 5.0-7.4 | | 138.0 | dimethylarsinic acid |
| SSC | 7.0 | 6.5-7.5 | | 189.1 | saline sodium citrate |
| MES | 6.15 | 5.5-6.7 | −0.011 | 195.2 | 2-(N-morpholino)ethanesulfonic acid |
| Succinic acid | 7.4 ( | 7.4-7.5 | | 118.09 | 2(R)-2-(methylamino)succinic acid |
| Bicine | 8.35 | 7.6-9.0 | −0.018 | 163.2 | N,N-bis(2-hydroxyethyl)glycine | nucleic acids. The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" "non-naturally occurring" or "non-native" as used herein refers to a material that is not found in nature or that has been structurally modified or synthesized by man.

The term "extracted nucleic acid" refers to a nucleic acid that (1) has been separated from at least about 50 percent of proteins, lipids, carbohydrates or other materials with which it is naturally found when total DNA is isolated from the source cells, (2) is not linked to all or a portion of a polynucleotide to which the "extracted nucleic acid" is linked in nature. Preferably, the isolated or extracted nucleic acid molecule of the present invention is substantially free from any other contaminating nucleic acid molecule(s) or other contaminants that are found in its natural environment.

Methods of Amplifying Nucleic Acids

The methods of the invention comprise amplifying the nucleic acid that is extracted from a microorganism or cell adhered to or entrapped within the polymer. The term "amplification method" refers to any method that increases the number of copies of a particular fragment of a nucleic acid sequence through replication of the fragment. These methods are typically carried out using thermal cycling instruments.

Polymerase chain reaction (PCR) is the most common nucleic acid amplification method using at least two primers and a DNA polymerase. Real-time PCR, also called quantitative PCR or qPCR, is a very sensitive method of amplifying and quantization of nucleic acids. Real-time PCR detects the products of nucleic acid amplification during the course of the reaction, and is generally considered to be more accurate than end-point PCR for determining initial target copy number.

Other nucleic acid amplification methods include strand displacement (SDA) which uses a stand-displacing DNA polymerase, isothermal amplification methods such as helicase-dependent amplification (HDA) and isothermal reverse transcription-thermophilic helicase-dependent amplification (RT-tHDA), rolling circle amplification (RCA) which is a unidirectional nucleic acid replication that can synthesize multiple copies of circular nucleic acids, loop-mediated isothermal amplification (LAMP) which uses a single temperature incubation for amplification, ligase chain reaction (LCA) which refers to the a nucleic acid amplification method that uses a thermostable DNA ligase and a thermostable DNA polymerase to amplify a target nucleic acid, nucleic acid sequence-based amplification (NASBA) is a one step isothermal process for amplifying RNA and vitro transcription. These methods may be carried out using techniques standard in the art. The invention also contemplates using sequencing analysis to confirm the identity of DNA fragments amplified using PCR.

In the methods of the invention, PCR may be carried out using a "PCR reaction mixture" which is a mixture suitable for carrying out PCR. The PCR reaction mixture will contain a suitable amount of a thermostable DNA polymerase, a linear or circular template DNA, preferably double-stranded DNA, to be amplified, a pair of oligonucleotide primers such that one of the primers is configured for annealing to one strand of the template and the other primer is configured for annealing to the other or complementary strand of the template, ATP, suitable amounts of each of the four deoxyribonucleoside triphosphates (dNTPs), and buffers, salts such as $MgCl_2$, preservatives, reducing agents, and water as may be required.

The oligonucleotide primers may be designed to specifically amplify a nucleic acid specific for genes of interest or gene that identifies a particular microorganism. When designing the oligonucleotide primers, the length of a primer depends upon its (A+T) content, and the Tm of its partner. In addition, the primer should be complex enough to decrease the likelihood of the primer annealing to sequences other than the chosen target. The methods of the invention may utilize primers ranging in length from 10-30 nucleotides; preferably the primers will be 17 nucleotides in length. Generally, a 40%-60% G+C content is recommended for the primers, avoiding internal secondary structure and long stretches of any one base. In addition, primers should not anneal to regions of secondary structure (within the target) having a higher melting point than the primer.

The oligonucleotide primers may be universal primers that amplify a nucleic acid sequence that is present in all types of a particular microorganism such as universal primers that are specific for any type of bacteria, fungi, virus or protozoa, for example primers for bacterial ribosomal 16S rRNA gene. For example, universal primers may be specific for a particular type of bacteria such as universal primers specific for anaerobic bacteria, universal primers specific for aerobic bacteria, universal primer specific for gram-negative bacteria or universal primers specific for gram-positive microorganisms. Furthermore, the universal primers may be specific for a particular genus of microorganism, for example, universal primers that amplify a nucleic acid sequence specific for streptococci, or the universal primer may be specific for a particular species of microorganism, for example universal primers that amplify a nucleic acid sequence specific for *Streptococcus mutans*, universal primers may be specific for a particular strain of microorganism, for example universal primers that amplify a nucleic acid sequence specific for *Streptococcus mutans* MT8148.

Deoxyribonucleoside triphosphates (dNTPs) include 2'-deoxyadenosine 5'-triphosphate (dATP), 2'-deoxycytidine 5'-triphosphate (dCTP), 2'-deoxyguanosine 5'-triphosphate (dGTP), and 2'-deoxythymidine 5'-triphosphate (dTTP). Generally, the concentration of dNTP in the PCR reaction is about 200 µM. It is important to keep the four dNTP concentrations above the estimated Km of each dNTP (10 µM-15 µM) and balanced for best base incorporation. Lowering the concentrations of dNTP and magnesium ion by an equal molar concentration can improve fidelity. Modified dNTPs (dig-11-dUTP, 5-bromo-dUTP, inosine, biotin-11-dUTP, biotin-16-dUTP and 7-deaza dGTP) and 2'-deoxyuridine 5'-triphosphate (dUTP) also may be used.

Furthermore, in addition to PCR and other amplification methods, the extracted nucleic acids may be analyzed using any conventional assay to identify the source or the presence/expression of a particular sequence. These assays may be carried out in place of an amplification method or in combination with an amplification method. Exemplary assays include conventional and pulsed-field Southern blot, Northern blot, denaturing gradient gel electrophoresis, dot blot hybridization, slot blot hybridization, microarrays. Exonuclease activity, Fluorescence In Situ Hybridization, (FISH) or in situ localization by repressor binding.

Microorganisms

The invention provides for methods of detecting of detecting microorganisms adhered to or entrapped in polymers malleable in a living organism. In addition, the invention provides for methods of determining the microbe profile of a sample of saliva from a living organism. A profile of the microbes of a saliva sample may be used to determine susceptibility or risk of the organism for developing dental caries or periodontal disease regardless if the microbes are currently causing an infection. Furthermore, the methods of the invention may be used for quality control methods to determine if a polymer is susceptible or resistant to attachment or entrapment of microbes.

"Microorganisms" or "microbes" refer to microscopic organisms which may be single celled or multicellular organisms, and may by pathogenic or commensal to the host organism. The invention provides for methods of detecting and quantitating microorganisms adhered to or entrapped within a polymer that is malleable in a living organism and these microorganisms include bacteria, viruses, fungi and protozoa.

The bacteria may be gram negative or gram positive bacteria, and anaerobic or aerobic bacteria. The invention particularly contemplates methods of detecting oral bacteria such as commensal oral bacteria and pathogenic oral bacteria such as *streptococci, lactobacilli, staphylococci, corynebacteria, actinomcyes* sp., *fusobacterium* sp. and various anaerobes in particular *bacteroides*. Exemplary oral bacteria include *Streptococcus mutans, Streptococcus oralis, Streptococcus salivarius, Actinomyces naeslundii, Streptococcus sanguinis, Porphyromomas gingivalis, Porphymomas intermedia, Bacteroides forsythus, Tanneraella. forsythia, Campylobacter rectus, Eubacerium nodatum, Peptostreptococcus micros, Streptococcus intermedius, Aggregetibacter actinomycetemcomitans, Treponema denticola, Eikenella corrodens, Capnocytophaga gingivalis, Streptococcus gordonii, Veillonella parvula, Fusobacterium nucleatum, Prevotella intermedia, Lactobacillus salivarius, Streptococcus salivarius* and *Streptoococus sobrinus*

The virus may be a member of the Herpesvirus family such as the Human Herpes Virus (HHV) including HHV-1 (also known as herpes simplex virus (HSV)-1), HHV-2 (HSV-2), HHV-3 (also known as varicella-zoster virus), HHV-4 (Epstein-Barr virus), HHV-5 (cytomegalovirus), HHV-6, HHV-7 and HHV-8.

The virus may be a member of the Picornaviridae family (*Enterovirus* genus) such as poliovirus, group A coxsackievirus, group B coxsackievirus, echovirus. In particular, the virus may cause hand-foot-mouth disease such as coxsackievirus A16, A5, A7, A10, B2 and B5, a virus that causes herpangina such as coxsackievirus A1-6, A8, A10, and A22 and *Enterovirus* 71 (EV-71).

The virus may be a member of the Papovaviridae family such as the Human Papillomavirus family (HPV) including HPV-16, HPV-18, HPV-33 and HPV-35. The virus may be a member of the Paramyoxvirus family (Rubularivurs genus) such as mumps virus, Newcaastle disease virus, human parainfluenza virus type 2, 4a and 4b. The virus may be a member of the Paramyxovirus family (Morbillivirus genus). In addition, the virus may be a member of the Togavirus family (Rubivirus genus). The virus may be also be canine oral Papilloma virus, feline calicivirus, and feline herpesvirus The virus may also be an influenza virus such as human influenza virus A such as H1N1 and H3N3, human influenza virus B and human influenza virus C. The virus can be a virus that causes the common cold such as rhinovirus.

Certain herpes viruses (herpes simplex and varicella-zoster virus, the cause of chickenpox and shingles) are known causes of gingivitis. Other herpes viruses (cytomegalovirus and Epstein-Barr) may also play a role in the onset or progression of some types of periodontal disease, including aggressive and severe chronic periodontal disease. All herpes viruses go through an active phase followed by a latent phase and possibly reactivation. These viruses may cause periodontal disease in different ways, including release of tissue-destructive cytokines, overgrowth of periodontal bacteria, suppressing immune factors, and initiation of other disease processes that lead to cell death.

The methods of the invention may detect a fungus such as *Candida* e.g. *Candida albicans, Aspergillus, Cryptococcus neoformans, Cryptococcus gattii, Histoplasma capsulatum, Blastomyces dermatitidis, Paracoccidioides brasiliensis, Coccidiodes immites* and *Zygomycota*.

The methods of the invention may detect protozoa such as *Entamoeba gingivalis* and *Trichomonas tenax*.

The invention contemplates detecting microorganisms that cause or are related to the oral diseases and disorders such as periodontal disease (inflammation or infection of gum tissue) such as chronic periodontitis and acute adult periodontitis, gingivitis, such as acute necrotizing ulcerative gingivitis, Vincent angina, dental caries, herpesvirus infection, primary herpetic gingivostomatitis, or oral herpes (cold sores and canker sores), genital herpes, varicella-zoster virus infection e.g. chicken pox or shingles, influenza, common cold, venereal disease, mononucleosis, coxsackievirus infection such as hand-foot-mouth disease, herpangina, acute lymphonodular pharyngitis, mumps, measles (reubeola), rubella (German measles), African Burkitt lymphoma, nasopharyngeal carcinoma, oral hairy leukoplakia, roseola infantum, Karposi sarcoma, Candidiasis, acute pseudomemranous candidosis (thrush), acute atrophic (erythematous) candidosis, chronic hyperplastic candidosis, and chronic atrophic (erythematous) candidosis, aspergillosis, cryptococcosis, Histoplasmosis (also known as Cave disease, Darling's disease, Ohio valley disease, Reticuloendotheliosis, Spelunker's Lung and Caver's disease, Blastomycosis (also known as North American blastomycosis, Blastomycetic dermatitis, and Gilchrist's disease) Paracoccidioidomycosis (also known as Brazilian blastomycosis, South American blastomycosis, Lutz-Splendore-de Almeida disease and Paracoccidioidal granuloma), mucormycosis (after Mucorales), phycomycosis (after Phycomycetes) and basidiobolomycosis (after Basidiobolus) and zygomycosis (mucormycosis). The invention also provides for methods of diagnosing any condition, disease or disorder that are caused by or related to the presence of a microorganism adhered to or entrapped within the polymer that is malleable in a living organism.

Mammalian Cells

Any of the methods of the invention may also be used to detect nucleic acids from a mammalian cell, such as a human cells, canine cells, feline cells, murine cells, rat cells, bovine cells, equine cells, sheep cells, goat cells, primate cells, cells from aquatic mammals such as whales and dolphins and cells from other exotic mammals, that is adhered to or entrapped within a polymer. The mammalian cells that may be detected include epithelial cells, squamous cells, fibroblasts, keratinocytes, odontoblasts, ameloblasts, cells within a taste bud such as sensory cells, support (or sustentacular) cells, stem cells, basal cells, cells within the salivary gland such as serous cells and mucous cells, Furthermore, the cells may be cancer cells such from a tumor that has developed on the surface of the tongue, mouth, lips, pharynx, tonsils or gums such as oral squamous cell carcinoma, salivary gland adenocarcinoma, mucoepidermoid carcinoma, adenoid cystic carcinoma, sarcomas (tumors arising from bone, cartilage, fat, fibrous tissue or muscle) lymphoma or melanoma. The cells am be precancerous cells from subjects suffering from precancerous conditions such as leukoplakia or erythroplakia.

Kits

The invention also provides for kits to carry out the methods of the invention. In particular, the invention provides for kit comprising components for detection and/or quantification of nucleic acids from a cell or microorganism adhered to or entrapped within a polymer according to any of the method of the invention. The kits will comprise oligonucleotide primers for amplifying a fragment of the nucleic acid specific for a microorganism of interest, a mammalian cell, such as human cells, or a cancer cell. The kits may further comprise universal forward and/or reverse primes for amplifying the nucleic acid. The kits may also comprise instructions for carrying out the methods of the invention.

The kits of the invention may also comprise the components necessary to carry out PCR or other amplification methods. For example, the kit may contain one or more of the following: Taq polymerase or another thermostable polymerase, ATP, suitable amounts of each of the four deoxyribonucleoside triphosphates (dNTPs), and buffers, salts such as $MgCl_2$, preservatives, reducing agents or water.

Kits may also comprise any the components necessary to carry out the detection assays such as the organic solvent and a buffered solution, such as chloroform and/or Tris buffer. The kits may comprise buffers, loading dyes, gels, molecular weight markers, membranes, filters, blocking buffers and detection reagents for Northern Blot analysis, Southern Blot analysis, slot-blot analysis or in situ hybridization analysis and any other methods convention in the art, such as those techniques.

Other aspects and advantages of the present invention will be understood upon consideration of the following illustrative example.

EXAMPLES

Example 1 describes the quantification of bacteria adhered to finger chewed chewing gum, Example 2 described the quantification of bacteria adhered to chewing gum in vivo, and Example 3 describes an additional experiments that to quantify bacteria which adhere to chewing gum in vivo.

Example 1

Quantification of Bacteria Adhered to or Entrapped within Chewing Gum In Vivo

A further study was carried out to demonstrate that chewing gum can remove bacteria from the oral cavity and the bacterial nucleic acids can be extracted.

Five healthy human volunteers (1 male, 4 female, aged 27 to 56 years) gave their written informed consent to participate in the this study. Inclusion criteria for the study were that each volunteer was in good health and have their permanent teeth with at least 16 natural elements. Exclusion criteria were the use of antibiotics or mouth rinse in the month prior to the study. Furthermore, volunteers did not use antibiotics, mouth rinse and other chewing gum types during the study. All experiments were carried out in duplicate.

Next, volunteers were asked to chew the two different gum types for varying amounts of time up to 10 minutes and the number of bacteria chewed in were determined in terms of CFUs using sonication of chewed gum tabs in terms of arbitrary units, as obtained using qPCR of bacterial DNA isolated from chewed gum tabs dissolved in chloroform. Determination of numbers of bacteria, using both methods, yielded an initial peak of incorporated amount of bacteria shortly after chewing. As chewing time increased, up to 10 minutes, bacterial incorporation decreased (FIG. 1).

On separate days volunteers were asked to chew 1.5 g of each type of chewing gum for 0.5, 1, 3, 5 or 10 minutes. Chewing time was randomly assigned and took place at the same point of time during the day. After chewing, the gum was spit in a polystyrene cup with 10 ml sterile water, after which the chewed gum put into a Teflon mould and sonicated, as described in Example 1 for finger-chewed gums. Resulting suspensions were plated on blood agar plates (Bloodagar base no. 2 40 g/L, Hemin 5 mg/L, Menadion 1 mg/L, sheep blood 50 ml/L) and the numbers of CFUs were determined after incubation for 7 days at 37° C. under anaerobic conditions (5-10% $H_2$, 10% $CO_2$, 80% $N_2$) (Concept 400 anaerobic workstation, Ruskinn Technology Ltd., Pencoed, UK).

In a separate run of experiments five healthy volunteers (4 male, 1 female) chewed 1.5 g of each type of chewing gum for 0.5, 1, 3, 5 or 10 minutes. Again the chewed gum was spit in a polystyrene cup with 10 ml sterile water after which it was dissolved in a sterile centrifuge tube with 5 ml of chloroform (67-66-3, Fisher Scientific, Waltham, USA) and 3 ml of TE buffer (AM9849, Ambion®-LifeTechnologies™, Carlsbad, USA). Tubes were shaken for at least 30 minutes to completely dissolve the gum. The resulting suspension was centrifuged for 10 minutes to remove large particles and gum base from the aqueous top layer.

For the qPCR analysis, a master mix was used consisting of 1000 µl PCR-mix (SsoFast™ EvaGreen® Supermix, Bio-rad, Hercules, USA), 500 µl of DNA free water (Fisher Scientific, Waltham, USA) and 250 µl of primer mix. The latter being a solution of 270 µL DNA free water with 15 µL of both forward and backward validated primers for 9 specific bacterial species. Details for the primers are provided in Table 2 below.

TABLE 2

| Bacteria | Sequence (5→3) | Direction | BP Length | Target | Reference |
|---|---|---|---|---|---|
| Species Specific Primers | | | | | |
| Porphyromonas gingivalis | CGGACTAAAACCGCAT ACACTTG (SEQ ID NO: 1) | forward | 110 | 16s rDNA | Price, 2007 |
| | GGTGAGCCGTTACCTCACCA (SEQ ID NO: 2) | reverse | | 16s rDNA | Price, 2007 |

TABLE 2-continued

| Bacteria | Sequence (5→3) | Direction | BP Length | Target | Reference |
|---|---|---|---|---|---|
| Fusobacterium nucleatum | CGCAGAAGGTGAAAGT CCTGTAT (SEQ ID NO: 3) | forward | 101 | 16s rRNA | Kato, 2005 |
| | TGGTCCTCACTGATTCA CACAGA (SEQ ID NO: 4) | reverse | | 16s rRNA | Kato, 2005 |
| | TGCGATAAGCCTAGAT AAGTTGCA (SEQ ID NO: 5) | forward | 70 | ISR | Price, 2007 |
| | CTTAATAGATTGCTCCA TTCGGAAA (SEQ ID NO: 6) | reverse | | ISR | Price, 2007 |
| Tannerella forsythia | ATCCTGGCTCAGGATGAACG (SEQ ID NO: 7) | forward | 225 | 16s rRNA | Kato, 2005 |
| | TACGCATACCCATCCGCAA (SEQ ID NO: 8) | reverse | | 16s rRNA | Kato, 2005 |
| | GAAACCTGCCCGCAACAGA (SEQ ID NO: 9) | forward | 71 | 16s rDNA | Price, 2007 |
| | TGCGGAACCCCTGTTTTATG (SEQ ID NO: 10) | reverse | | 16s rDNA | Price, 2007 |
| Treponema denticola | AGAGCAAGCTCTCCCTTACCGT (SEQ ID NO: 11) | forward | 105 | 16s rRNA | Kato, 2005 |
| | TAAGGGCGGCTTGAAATAATGA (SEQ ID NO: 12) | reverse | | 16s rRNA | Kato, 2005 |
| | TAATACCGAATGTGCT CATTTACAT (SEQ ID NO: 13) | forward | 316 | 16s rDNA | Kirakodu, 2008 |
| | TCAAAGAAGCATTCCC TCTTCTTCTTA (SEQ ID NO: 14) | reverse | | 16s rDNA | Kirakodu, 2008 |
| Lactobacillus salivarius | AGCCGATGAAGGACGTGACT (SEQ ID NO: 15) | forward | 72 | ISR | Price, 2007 |
| | GGAAATCTCCGGATCA TAGTTTACTTA (SEQ ID NO: 16) | reverse | | ISR | Price, 2007 |
| Streptococcus mutans | TGGGACGCAAGGAACA (SEQ ID NO: 17) | forward | 58 | 16s rDNA | Price, 2007 |
| | CCCGTTCGCGACTCAAGA (SEQ ID NO: 18) | reverse | | 16s rDNA | Price, 2007 |
| | TCGCGAAAAAGATAAA CAAACA (SEQ ID NO: 19) | forward | 479 | | Psoter, 2010 |
| | GCCCCTTCACAGTTGGTTAG (SEQ ID NO: 20) | reverse | | | Psoter, 2010 |
| Streptococcus sobrinus | GGACTTGCTCCAGTGTT ACTAATGAG (SEQ ID NO: 21) | forward | 70 | 16s rDNA | Price, 2007 |
| | CCGCTATCAGGCAGGTTACC (SEQ ID NO: 22) | reverse | | 16s rDNA | Price, 2007 |
| Aggregatibacter actinomycete- mcomitans | ATT GGG GTT TAG CCC TGG T (SEQ ID NO: 23) | forward | 194 | | Psoter, 2010 |
| | GGCACAAACCCATCTCTGA (SEQ ID NO: 24) | reverse | | | Psoter, 2010 |
| | CTAGGTATTGCGAAACAATTTG (SEQ ID NO: 25) | forward | 262 | 16s rDNA | Kirakodu, 2008 |
| | CCTGAAATTAAGCTGGTAATC (SEQ ID NO: 26) | reverse | | 16S rDNA | Kirakodu, 2008 |
| | ATGGTTGTAGGCAATGGAAGAAC (SEQ ID NO: 27) | forward | ***64 | ISR | Price, 2007 |
| | CACCTGAGCTACAGACCCAACA (SEQ ID NO: 28) | reverse | | ISR | Price, 2007 |
| Streptococcus salivarius | GCAGCAGTAGCAGAGACGCT (SEQ ID NO: 29) | forward | 331 | | Garnier, 1997 |
| | CACGGACGTCTTCAGTACTG (SEQ ID NO: 30) | reverse | | | Garnier, 1997 |
| Prevotella intermedia | GTGGCGCGTATTTTATGTATGTG (SEQ ID NO: 31) | Forward | 64 | ISR | Price 2007 |
| | ATCCGCCATACGCCCTTAG (SEQ ID NO: 32) | Reverse | | | |

TABLE 2-continued

| Bacteria | Sequence (5→3) | Direction | BP Length | Target | Reference |
|---|---|---|---|---|---|
| *Actinomyces naeslundii* (early colonizer bacteria found in plaque) | TCGAAACTCAGCAAGTAGCCG (SEQ ID NO: 33) | Forward | 96 | ISR | Suzuki 2005 |
| | AGAGGAGGGCCACAAAAGAAA (SEQ ID NO: 34) | Reverse | | | |
| Genus Specific Primers | | | | | |
| *Actinomycetes* sp. | GGATGAGCCCGCGGCCTA (SEQ ID NO: 35) | Forward | | | Heuer |
| | CGGCCGCGGCTGCTGGCACGTA (SEQ ID NO: 36) | Reverse | | | |
| *Fusobacterium* sp. | CGCAGAAGGTGAAAGT CCTGTAT (SEQ ID NO: 37) | Forward | | | Suzuki 2005 |
| | TGGTCCTCACTGATTCA CACAGA (SEQ ID NO: 38) | Reverse | | | |
| *Prevotella* sp. | CCAGCCAAGTAGCGTGCA (SEQ ID NO: 39) | Forward | | | Suzuki 2005 |
| | TGGACCTTCCGTATTACCGC (SEQ ID NO: 40) | Reverse | | | |
| *Veillonella* sp. | CCGTGATGGGATGGAAACTGC (SEQ ID NO: 41) | Forward | | | Periasamy 2009 |
| | CCTTCGCCACTGGTGTTCTTC (SEQ ID NO: 42) | Reverse | | | |
| *Streptococcus* sp. | AGAGTTTGATCCTGGCTCAG (SEQ ID NO: 43) | Forward | | | Fouad 2002 |
| | GACCGTCACAGTATG AACTTTCC (SEQ ID NO: 44) | Reverse | | | |
| *Lactobaciullus* sp. | CTCAAAACTAAACAAAGTTTC (SEQ ID NO: 45) | Forward | | | Dubernet 2002 |
| | CTTGTACACACCGCCCGTCA (SEQ ID NO: 46) | Reverse | | | |
| Universal Primers | | | | | |
| UnivF | CCT ACG GGA GGC AGC AG (SEQ ID NO: 47) | Forward | | 16s rDNA | Muyzer et al., 1993 |
| | ATT ACC GCG GCT GCT GG (SEQ ID NO: 48) | Reverse | | | |

In a 96-well PCR plate (MSP-9601, Bio-rad, Hercules, USA) 2.5 µL of sample, taken from the aqueous solution, was mixed with 17.5 µL of master mix. Subsequently qPCR was performed on a thermocycler (CFX96, Bio-rad, Hercules, USA), according to a 2 step amplification (95.0° C. for 10 seconds, 55.0° C. for 30 seconds) making 39 cycles and a melt curve (65° C. to 95.0° C.). Plates included positive controls, depending on the primer sets and negative controls; no DNA and no primer. Results are expressed as fold expression and compared within experiments, whilst bacterial counts are expressed as arbitrary units (AU).

According to these in vivo experiments, the amount of bacteria trapped in the gum is estimated to be $1 \times 10^7$, depending on the time of chewing. It is estimated that whole saliva harbors $10^8$-$10^9$ microorganisms (Burt et al. Journal of the American Dental Association 127: 190-196, 2006), meaning 1-10% of the salivary bacteria can actually be trapped and removed from the oral cavity by chewing gum.

Example 2

Additional Experiments to Quantify Bacteria Adhered or Entrapped within to Chewing Gum In Vivo Further experiments were carried out to determine the minimum time necessary to saturate chewing gum with bacteria and to quantify the bacteria that adheres to the chewing gum. The methods were generally carried out as described above in Example 1.

Five subjects were asked to chew spearmint chewing gum over 2 weeks. The subjects were only allowed to chew one piece of gum per day. The chewed cud was stored in 15 mL sterile falcon tube until the PCR analysis. These samples are described below in Table 3.

TABLE 3

Chew Times and Cud Weights

| Tube No. | Time (min) | Participant | Tube Weight (g) | Tube + Cud (g) | Cud Weight (g) |
|---|---|---|---|---|---|
| 1 | 1 | MC | 6.6793 | 8.1207 | 1.4414 |
| 2 | 2 | MC | 6.4792 | 7.6965 | 1.2173 |
| 3 | 4 | MC | 6.4359 | 7.4894 | 1.0535 |
| 4 | 6 | MC | 6.622 | 7.624 | 1.0020 |
| 5 | 8 | MC | 6.6771 | 7.6319 | 0.9548 |
| 6 | 10 | MC | 6.6517 | 7.642 | 0.9903 |
| 7 | 15 | MC | 6.4783 | 7.4203 | 0.9420 |
| 8 | 20 | MC | 6.5048 | 7.4956 | 0.9908 |
| 9 | 1 | KG | 6.5266 | 7.8258 | 1.2992 |
| 10 | 2 | KG | 6.454 | 7.4417 | 0.9877 |
| 11 | 4 | KG | 6.4479 | 7.44832 | 1.0004 |
| 12 | 6 | KG | 6.4538 | 7.4224 | 0.9686 |
| 13 | 8 | KG | 6.6643 | 7.6274 | 0.9631 |
| 14 | 10 | KG | 6.4792 | 7.4342 | 0.9550 |
| 15 | 15 | KG | 6.6426 | 7.5565 | 0.9139 |
| 16 | 20 | KG | 6.4492 | 7.3656 | 0.9164 |
| 17 | 1 | DM | 6.6076 | 7.9626 | 1.3550 |
| 18 | 2 | DM | 6.629 | 7.7507 | 1.1217 |
| 19 | 4 | DM | 6.4244 | 7.3556 | 0.9312 |
| 20 | 6 | DM | 6.526 | 7.5154 | 0.9894 |
| 21 | 8 | DM | 6.4762 | 7.4282 | 0.9520 |
| 22 | 10 | DM | 6.4368 | 7.3738 | 0.9370 |
| 23 | 15 | DM | 6.45 | 7.3292 | 0.8792 |
| 24 | 20 | DM | 6.6163 | 7.5151 | 0.8988 |
| 25 | 1 | LT | 6.5703 | 7.9166 | 1.3463 |
| 26 | 2 | LT | 6.4708 | 7.5633 | 1.0925 |
| 27 | 4 | LT | 6.4821 | 7.4685 | 0.9864 |
| 28 | 6 | LT | 6.4996 | 7.4297 | 0.9301 |
| 29 | 8 | LT | 6.4984 | 7.4563 | 0.9579 |
| 30 | 10 | LT | 6.5032 | 7.4535 | 0.9503 |
| 31 | 15 | LT | 6.4529 | 7.3619 | 0.9090 |
| 32 | 20 | LT | 6.4613 | 7.3619 | 0.9006 |
| 33 | 1 | DL | 6.4857 | 8.0274 | 1.5417 |
| 34 | 2 | DL | 6.6997 | 7.8856 | 1.1859 |
| 35 | 4 | DL | 6.5313 | 7.5762 | 1.0449 |
| 36 | 6 | DL | 6.5426 | 7.5591 | 1.0165 |
| 37 | 8 | DL | 6.5799 | 7.556 | 0.9761 |
| 38 | 10 | DL | 6.4366 | 7.4013 | 0.9647 |
| 39 | 15 | DL | 6.4539 | 7.3837 | 0.9298 |
| 40 | 20 | DL | 6.6729 | 7.5753 | 0.9024 |

For analysis, the frozen gum cuds were removed from the freezer and allowed to come to room temperature. TE buffer (3 ml) and chloroform (5 ml) were added to the tube containing a gum cud. The samples were mixed for 30 minutes and once the gum cud was completely dissolved, the samples were centrifuged at 4500 rpm for 10 minutes. Subsequently, 2 ml of aqueous top layer was removed and analyzed by PCR.

PCR was carried out using the SsoFast kit according the manufacturer's instructions with a forward and reverse universal primer. The reaction was carried out as follows: 95.0° C. for 3 minutes, 95.0° C. for 10 seconds, 55.0° C. for 30 seconds followed by the following cycle repeated 39 times: 95.0° C. for 10 seconds, then Melt curve 65.0° C. to 95.0° C.: Increment 0.5° C. for 5 seconds.

According to the result in the Table 3, about 400 bacterial counts adhered to the chewing gum after one minute of chewing. As show in FIG. 1, the amounts of bacteria adhered to the chewing gum slightly decreased as chewing time progressed to 20 minutes of chewing.

This study is further evidence that the methods of the invention can detect and quantify oral bacteria that has adhered to chewing gum.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed:

1. A method of extracting nucleic acids from a polymer that is malleable within a living organism, the method comprising the steps of:
   a) contacting the polymer with i) chloroform and ii) a buffer solution, and
   b) separating the chloroform from the buffer solution, wherein the nucleic acids extracted from the polymer are contained within the buffer solution.

2. The method of claim 1 further comprising the step of identifying the source of the nucleic acids extracted from the polymer.

3. The method of claim 1 further comprising the step of quantifying the nucleic acids extracted from the polymer.

4. The method of claim 2 wherein the identifying step or the quantifying step is carried out using an amplification method to amplify the nucleic acids.

5. The method of claim 2 wherein the source of the nucleic acids is identified using polymerase chain reaction.

6. The method of claim 3 wherein the nucleic acids are quantified using quantitative polymerase chain reaction.

7. The method of claim 1 wherein the polymer is completely dissolved by the chloroform.

8. The method of claim 1 wherein the nucleic acids are extracted from an internal surface of the polymer.

9. The method of claim 1 wherein at least 90% of the nucleic acids adhered to or entrapped within the polymer are extracted.

10. The method of claim 1 wherein the source of the nucleic acids is a microorganism.

11. The method of claim 1 wherein the source of the nucleic acids is a mammalian cell, optionally wherein the mammalian cell is an epithelial cell, a squamous cell, a fibroblast or a keratinocyte.

12. The method of claim 11 wherein the mammalian cell is a cancer cell.

13. A method of detecting microorganisms adhered to or entrapped within a polymer malleable in a living organism, the method comprising the steps of:
   a) dissolving at least a portion of the polymer in chloroform and a buffer solution,
   b) separating the chloroform from the buffer solution, wherein nucleic acids extracted from the microorganisms are contained within the buffer solution, and
   c) amplifying the nucleic acids using at least one oligonucleotide primer specific for the microorganism.

14. The method of claim 13 further comprising the step of quantitating the microorganism adhered to or entrapped within the polymer.

15. The method of claim 13 wherein the nucleic acid is amplified using polymerase chain reaction.

16. The method of claim 13 wherein the nucleic acid is amplified using polymerase chain reaction.

17. A method of identifying malleable polymers resistant to adherence of microorganisms, the method comprising the steps of:
   a) contacting a malleable polymer with a microorganism under conditions that promote adherence,
   b) dissolving at least a portion of the polymer in chloroform and a buffer solution,
   c) separating the chloroform from the buffer solution, wherein nucleic acids extracted from the microorganism adhered to the polymer are contained within the buffer solution, and
   d) detecting the presence or absence of a nucleic acid specific for a microorganism in the buffer solution, wherein the absence of nucleic acids in the buffer solution is indicative of a polymer that is resistant to the attachment of the microorganism.

18. The method of claim 17 wherein the buffer solution is Tris buffer.

* * * * *